US009370539B2

(12) United States Patent
Scott

(10) Patent No.: US 9,370,539 B2
(45) Date of Patent: Jun. 21, 2016

(54) TOPICAL COMPOSITIONS AND METHODS FOR ALLEVIATING OR INHIBITING SYMPTOMS ASSOCIATED WITH CARPAL TUNNEL SYNDROME, ACID REFLUX, PSORIASIS, CARTILAGE NODULES, FIBROMYALGIA, AND DIABETES

(76) Inventor: Donald E. Scott, Rushville, OH (US)

( * ) Notice: Subject to any disclaimer, the term of this patent is extended or adjusted under 35 U.S.C. 154(b) by 391 days.

(21) Appl. No.: 11/917,015

(22) PCT Filed: Jun. 7, 2006

(86) PCT No.: PCT/US2006/022129
§ 371 (c)(1),
(2), (4) Date: Dec. 10, 2007

(87) PCT Pub. No.: WO2006/135635
PCT Pub. Date: Dec. 21, 2006

(65) Prior Publication Data
US 2008/0206377 A1      Aug. 28, 2008

Related U.S. Application Data

(60) Provisional application No. 60/689,590, filed on Jun. 10, 2005.

(51) Int. Cl.
*A01N 65/00* (2009.01)
*A61K 36/00* (2006.01)

(52) U.S. Cl.
CPC ..................................... *A61K 36/00* (2013.01)

(58) Field of Classification Search
CPC ....................................................... A61K 36/00
USPC ................................................ 424/777, 725
See application file for complete search history.

(56) References Cited

U.S. PATENT DOCUMENTS

| | | | |
|---|---|---|---|
| 4,626,529 A | | 12/1986 | Grollier |
| 5,888,984 A | | 3/1999 | Brown |
| 6,153,197 A | * | 11/2000 | Albazi et al. |
| 6,399,112 B1 | * | 6/2002 | Whittle et al. |
| 2002/0182260 A1 | | 12/2002 | Mak et al. |
| 2002/0197380 A1 | | 12/2002 | Mantius et al. |
| 2003/0104079 A1 | * | 6/2003 | Sakanaka et al. |
| 2003/0149107 A1 | * | 8/2003 | Sharma et al. |
| 2004/0162245 A1 | * | 8/2004 | Butler et al. |
| 2005/0100524 A1 | * | 5/2005 | Springstead |

FOREIGN PATENT DOCUMENTS

| | | | |
|---|---|---|---|
| BE | 851033 A | * | 5/1977 |
| WO | 0064472 | | 11/2000 |
| WO | 2004050059 A1 | | 6/2004 |
| WO | 2004091569 A2 | | 10/2004 |

OTHER PUBLICATIONS

Green, J. The Herbal Medicine-Maker's Handbook,: A Home Manual (2000). The Crossing Press, USA, pp. 276-278,280 and 284.*
Balch, PA. Prescription for Herbal Healing (2002). Penguin Putnam, Inc., USA; "Poultices", pp. 430.*
Wikipedia contributors, 'Fruit', Wikipedia, The Free Encyclopedia, Sep. 3, 2014, 03:13 UTC, <http://en.wikipedia.org/w/index.php?title=Fruit&oldid=623951882> [accessed Sep. 28, 2014].*
Wikipedia contributors, 'Flowering plant', Wikipedia, The Free Encyclopedia, Sep. 14, 2014, 20:10 UTC, <http://en.wikipedia.org/w/index.php?title=Flowering_plant&oldid=625562483> [accessed Sep. 28, 2014].*
Mayo Staff Clinc Staff, "Diseases and Conditions: Carpal tunnel syndrome", http://www.mayoclinic.org/diseases-conditions/carpal-tunnel-syndrome/basics/prevention/con-20030332?p=1.*
International Search Report, mailed Feb. 28, 2007.
Roy, S. et al., "Anti-angiogenic property of edible berries," Free Radic. Res., 36:9 (2002), 1023-1031 (Abstract only).

* cited by examiner

*Primary Examiner* — Michael Meller
(74) *Attorney, Agent, or Firm* — Wood, Herron & Evans, L.L.P.

(57) ABSTRACT

A composition for, and method of, alleviating or inhibiting one or more symptoms associated with carpal tunnel syndrome, acid reflux, psoriasis, cartilage nodules, fibromyalgia, diabetes, or hypoglycemia in a mammal. The composition includes a fruit-vegetable extract, the composition formulated for contact with the mammal's skin, the fruit-vegetable extract present in an amount effective to alleviate or inhibit one or more symptoms associated with carpal tunnel syndrome, acid reflux, psoriasis, cartilage nodules, fibromyalgia, diabetes, or hypoglycemia in the mammal. The method includes contacting the mammal's skin with a composition that includes a fruit-vegetable extract. The fruit-vegetable extract is present in an amount effective to alleviate or inhibit one or more symptoms associated with carpal tunnel syndrome, acid reflux, psoriasis, cartilage nodules, fibromyalgia, diabetes, or hypoglycemia in the mammal.

16 Claims, No Drawings

TOPICAL COMPOSITIONS AND METHODS FOR ALLEVIATING OR INHIBITING SYMPTOMS ASSOCIATED WITH CARPAL TUNNEL SYNDROME, ACID REFLUX, PSORIASIS, CARTILAGE NODULES, FIBROMYALGIA, AND DIABETES

FIELD OF THE INVENTION

The present invention pertains generally to compositions and methods for alleviating various symptoms of various conditions and, more particularly, to compositions and methods including fruit and/or vegetable extracts, that are applied to the skin to alleviate symptoms associated with various conditions.

SUMMARY OF THE INVENTION

The invention is directed to topical compositions and methods for alleviating or inhibiting one or more symptoms associated with carpal tunnel syndrome, acid reflux, psoriasis, cartilage nodules, fibromyalgia, diabetes, or hypoglycemia in a mammal. The compositions may include fruit and/or vegetable extracts, and are formulated for contact with the skin of the mammal. The fruit and/or vegetable extracts are present in the compositions in an amount effective to alleviate or inhibit one or more symptoms associated with carpal tunnel syndrome, acid reflux, psoriasis, cartilage nodules, fibromyalgia, diabetes, or hypoglycemia in the particular mammal.

The present invention is also directed to a method of alleviating or inhibiting one or more symptoms associated with carpal tunnel syndrome, acid reflux, psoriasis, cartilage nodules, fibromyalgia, diabetes, or hypoglycemia in a mammal, the method comprising the step of contacting the mammal's skin with a composition that includes a fruit-vegetable extract, the fruit-vegetable extract present in an amount effective to alleviate or inhibit one or more symptoms associated with carpal tunnel syndrome, acid reflux, psoriasis, cartilage nodules, fibromyalgia, diabetes, or hypoglycemia in the mammal.

DETAILED DESCRIPTION OF SPECIFIC ASPECTS OF THE INVENTION

The invention is directed to topical compositions and methods for alleviating or inhibiting one or more symptoms associated with carpal tunnel syndrome, acid reflux, psoriasis, cartilage nodules, fibromyalgia, diabetes, or hypoglycemia in a mammal. The compositions may include fruit and/or vegetable extracts, and are formulated for contact with the skin of the mammal. The fruit and/or vegetable extracts are present in the compositions in an amount effective to alleviate or inhibit one or more symptoms associated with carpal tunnel syndrome, acid reflux, psoriasis, cartilage nodules, fibromyalgia, diabetes, or hypoglycemia in the particular mammal. For the sake of convenience, the description below often uses words such as "person," "individual," or the like, instead of the word "mammal." However, such words should be interpreted as referring to any mammal, unless there is an explicit statement to the contrary. If desired, the compositions also may include ginseng, vitamins, shark cartilage, and/or other supplements.

If desired, a suitable fruit extract may include several ingredients. For example, a fruit extract may include fruit juice powder and pulp from apple, orange, pineapple, cranberry, peach, acerola cherry and *papaya*; bromelain, papain, lipase, amylase, protease, and cellulase; apple pectin, citrus pectin, date fiber, prune powder, glucomannan, citrus bioflavonoids, dried plant fiber, *Lactobacillus acidophilus*, anthocyanins, polyphenol catechins, *Dunaliella* saline, and indole carbinols. One such fruit extract is Juice PLUS+® Orchard Blend, commercially available from National Safety Associates, Inc. (also referred to as "NSA") of Memphis, Tenn.

If desired, a suitable vegetable extract may include several ingredients. For example, a vegetable extract may include vegetable juice powder and pulp from carrots, parsley, beets, kale, broccoli, cabbage, spinach, and tomato; lipase, amylase, protease, cellulase; beet fiber, barley bran, oat bran, cabbage fiber, glucomannan, plant cellulose, dried plant fiber, *Lactobacillus acidophilus*, anthocyanins, allicin, lycopene, polyphenol catechins, *Dunaliella* saline, and indole carbinols. One such vegetable extract is Juice PLUS+® Garden Blend, commercially available from National Safety Associates, Inc. (also referred to as "NSA") of Memphis, Tenn.

The compositions of the invention may be made as follows. Fruits and vegetables may be crushed, pulverized, squeezed, or otherwise manipulated, so as to form an extract. This extraction process may be performed at room temperature. For those compositions that include one or more additional ingredients (e.g., ginseng, vitamins, shark cartilage, and/or other supplements), the additional ingredient(s) may be mixed with the extract. Depending on the desired physical state of the composition, liquid may be removed from the extract or extract mix. For example, if a slurry or paste is desired, then some amount of liquid may be removed. If a powder or other solid is desired, then most, if not all, of the liquid may be removed. Liquid removal may be accomplished by any suitable method, with evaporation being one example. Also, if a composition of the invention is prepared as a powder, but a slurry or paste is later desired, a liquid (e.g., water or other suitable carrier or solvent) may be added to the powder to achieve the desired consistency.

When used for carpal tunnel syndrome, a composition may be applied directly to the affected wrist. For example, if a paste is used, the paste may be applied to the wrist, adjacent the palm of the hand. The application may be approximately ⅛ inch thick, and may extend about 3 inches in length. A bandage or other wrap then may be placed over the paste. A liquid (e.g., water) may be applied to the bandage or wrap; and the wrap (and underlying paste) may be kept moist throughout the treatment. If desired, three two-day treatments may be conducted, with five days between each such treatment. When the bandage or wrap is removed after a treatment, the underlying skin may be washed.

When used for acid reflux, a composition may be applied directly to the outside of the throat, at the area of acid irritation. For example, if a paste is used, the paste may be applied as a thin layer. A bandage or other wrap may then be placed over the paste. A liquid (e.g., water) may be applied to the bandage or wrap and the wrap (and underlying paste) may be kept moist throughout the treatment. If desired, the bandage or wrap may be worn for 24 hours. When the bandage or wrap is removed after the treatment, the underlying skin may be washed.

When used for psoriasis, a composition may be applied directly to the affected (e.g., outbreak) area. For example, if a paste is used, the paste may be applied as a thin layer. A bandage or other wrap then may be placed over the paste. A liquid (e.g., water) may be applied to the bandage or wrap, and the wrap (and underlying paste) may be kept moist throughout the treatment. If desired, the bandage or wrap may be worn for up to 48 hours. When the bandage or wrap is removed after the treatment, the underlying skin may be washed.

When used for cartilage nodules, a composition may be applied directly to the affected area (e.g., knee or other joint). For example, if a paste is used, the paste may be applied to the affected area; and the application may be approximately ⅛ inch thick. A bandage or other wrap may then be placed over the paste. A liquid (e.g., water) may be applied to the bandage or wrap, and the wrap (and underlying paste) may be kept moist throughout the treatment. If desired, the bandage or wrap may be worn for up to 48 hours. When the bandage or wrap is removed after a treatment, the underlying skin may be washed.

When used for fibromyalgia, a composition may be applied directly to the skin at the affected area. For example, a suspension, solution, or slurry may be made by mixing a powdered form of the composition with water. Examples of various ratios include one teaspoon of powder to ⅙ cup of water, and ½ teaspoon of powder to three teaspoons of water. The aqueous mixture then may be applied to the skin at the affected area. Advantageously, the mixture may be applied when the skin is well-hydrated—for example, after a shower, bath, or the like.

When used for diabetes and/or hypoglycemia, a composition may be applied directly to the skin. For example, a suspension, solution, or slurry may be made by mixing a powdered form of the composition with water. Examples of various ratios include one teaspoon of powder to ⅙ cup of water, and ½ teaspoon of powder to three teaspoons of water. The aqueous mixture then may be applied to the skin. Advantageously, the mixture may be applied when the skin is well-hydrated—for example, after a shower, bath, or the like.

While the present invention has been illustrated by a description of various embodiments, and while the illustrative embodiments have been described in considerable detail, it is not the intention of the inventor to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the inventor's general inventive concept.

What is claimed is:

1. A method of treating carpal tunnel syndrome in a human in need thereof consisting essentially of administering therapeutically effective amounts of bromelain and papain to said human in need thereof to effectively treat the carpal tunnel syndrome in said human in need thereof.

2. The method of claim 1, wherein the composition is in a dry form, and wherein the mammal's skin is contacted with the dry form.

3. The method of claim 2, wherein a fabric is positioned over the composition, wherein a substantial portion of the composition is positioned between the fabric and the skin of the human.

4. The method of claim 3, wherein a liquid is applied to the fabric.

5. The method of claim 4, wherein the fabric and the composition are kept moist throughout the treatment.

6. The method of claim 1, wherein the composition is in the form of a paste or slurry, and wherein the paste or slurry is contacted with the human's skin.

7. The method of claim 6, wherein a fabric is positioned over the paste or slurry, wherein a substantial portion of the paste or slurry is positioned between the fabric and the skin.

8. The method of claim 7, wherein the fabric and the paste or slurry are kept moist throughout the treatment.

9. A method of treating carpal tunnel syndrome in a human in need thereof consisting essentially of administering therapeutically effective amounts of bromelain, papain, pectin, citrus bioflavonoids, and lycopene to said human in need thereof to effectively treat the carpal tunnel syndrome in said human in need thereof.

10. The method of claim 9, wherein the composition is in a dry form, and wherein the mammal's skin is contacted with the dry form.

11. The method of claim 10, wherein a fabric is positioned over the composition, wherein a substantial portion of the composition is positioned between the fabric and the skin of the human.

12. The method of claim 11, wherein a liquid is applied to the fabric.

13. The method of claim 12, wherein the fabric and the composition are kept moist throughout the treatment.

14. The method of claim 9, wherein the composition is in the form of a paste or slurry, and wherein the paste or slurry is contacted with the human's skin.

15. The method of claim 14, wherein a fabric is positioned over the paste or slurry, wherein a substantial portion of the paste or slurry is positioned between the fabric and the skin.

16. The method of claim 15, wherein the fabric and the paste or slurry are kept moist throughout the treatment.

\* \* \* \* \*